United States Patent
Pierre et al.

(10) Patent No.: US 12,226,248 B2
(45) Date of Patent: Feb. 18, 2025

(54) DEVICE FOR AN X-RAY IMAGING SYSTEM

(71) Applicant: ECENTIAL ROBOTICS, Gières (FR)

(72) Inventors: Arnaud Pierre, Gières (FR); David Armand, Gières (FR)

(73) Assignee: ECENTIAL ROBOTICS, Gières (FR)

( * ) Notice: Subject to any disclaimer, the term of this patent is extended or adjusted under 35 U.S.C. 154(b) by 110 days.

(21) Appl. No.: 18/157,520

(22) Filed: Jan. 20, 2023

(65) Prior Publication Data

US 2023/0225688 A1 Jul. 20, 2023

(51) Int. Cl.
*A61B 6/00* (2024.01)
*A61B 6/10* (2006.01)
*A61B 6/40* (2024.01)

(52) U.S. Cl.
CPC ........... *A61B 6/48* (2013.01); *A61B 6/107* (2013.01); *A61B 6/4085* (2013.01)

(58) Field of Classification Search
None
See application file for complete search history.

(56) References Cited

U.S. PATENT DOCUMENTS

| | | | | |
|---|---|---|---|---|
| 11,253,322 | B2* | 2/2022 | Van Beek | A61B 34/20 |
| 11,278,355 | B2* | 3/2022 | Van Beek | A61B 90/39 |
| 12,053,247 | B1* | 8/2024 | Chiou | G06F 3/011 |
| 2012/0076371 | A1* | 3/2012 | Caruba | A61B 6/037 |
| | | | | 250/252.1 |
| 2013/0004042 | A1* | 1/2013 | Yang | A61B 6/032 |
| | | | | 382/131 |
| 2013/0235969 | A1* | 9/2013 | Winter | A61B 6/583 |
| | | | | 378/4 |
| 2013/0315374 | A1* | 11/2013 | Gertner | A61F 9/008 |
| | | | | 378/65 |
| 2016/0242724 | A1* | 8/2016 | Lavallee | A61B 90/39 |

(Continued)

FOREIGN PATENT DOCUMENTS

| | | |
|---|---|---|
| WO | 2016/138449 A1 | 9/2016 |
| WO | 2017/064254 A1 | 4/2017 |
| WO | 2021/165506 A1 | 8/2021 |

OTHER PUBLICATIONS

Extended European Search Report and Opinion for European Application No. 22315016.0, dated Jul. 15, 2022, 7 pages.

*Primary Examiner* — David P Porta
*Assistant Examiner* — Djura Malevic
(74) *Attorney, Agent, or Firm* — TraskBritt

(57) ABSTRACT

A device, as disclosed, may be suitable for use with a tomographic imager comprising an X-ray source and a plane detector that are movable in rotation. The device (e.g., radiopaque device) includes a registration phantom that includes several radiopaque markers and that is placeable along a part of the spine of a patient at a predetermined distance from a volume of interest to be imaged. Several radiopaque screens, integral with the registration phantom, include a lower face, an internal face oriented toward the registration phantom, and an external face oriented toward the X-ray source (410), respectively towards the detector. The radiopaque device is configured so that, when it is placed on the back of a patient, at least part of the X-rays that pass from the X-ray source to the plane detector through the registration phantom see their intensity attenuated by passing through the radiopaque screens.

16 Claims, 7 Drawing Sheets

(56) References Cited

U.S. PATENT DOCUMENTS

| | | | |
|---|---|---|---|
| 2019/0000564 A1* | 1/2019 | Navab | H04N 13/254 |
| 2022/0092800 A1* | 3/2022 | Toporek | A61B 6/4266 |
| 2022/0370152 A1* | 11/2022 | Lavallee | A61B 6/4085 |
| 2023/0106438 A1* | 4/2023 | Pierre | A61B 90/36 |
| | | | 606/117 |
| 2023/0165557 A1* | 6/2023 | Datta | A61B 6/584 |
| | | | 378/207 |
| 2023/0166127 A1* | 6/2023 | Vojan | A61N 5/1049 |
| | | | 378/65 |
| 2024/0245461 A1* | 7/2024 | Lavallée | A61B 17/00 |

\* cited by examiner

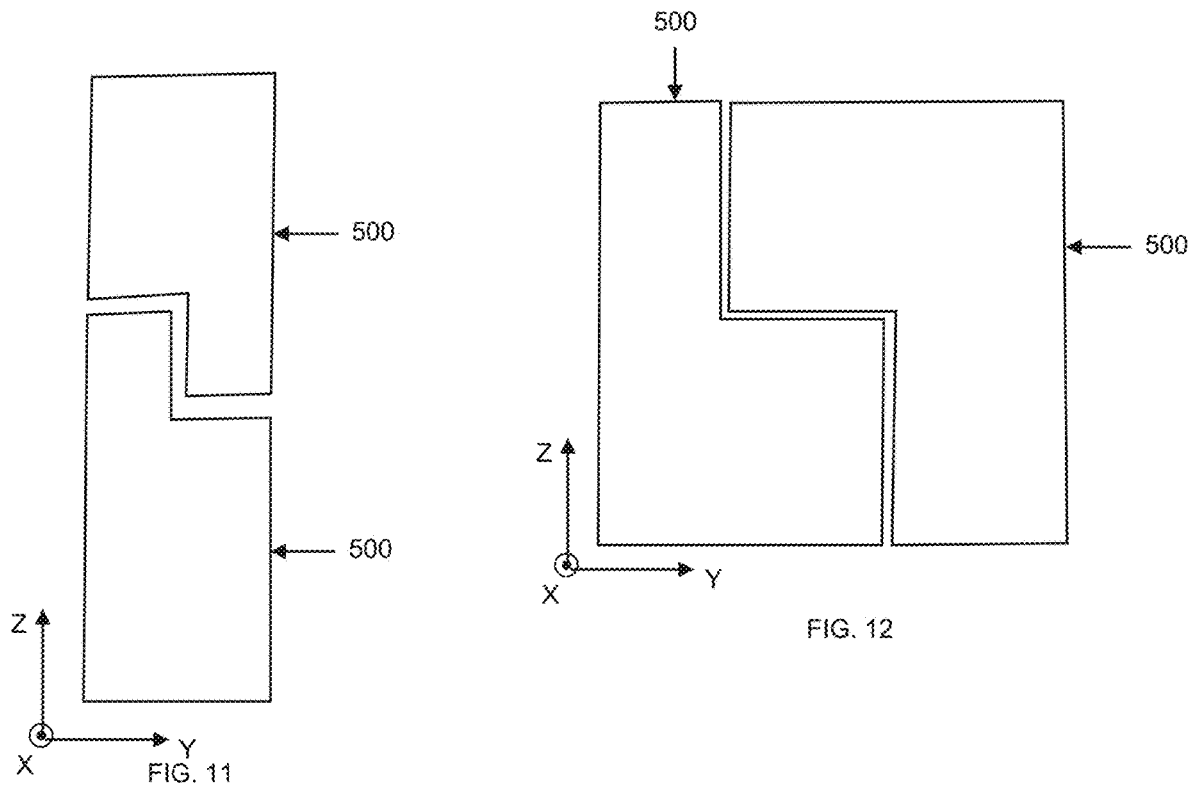

DEVICE FOR AN X-RAY IMAGING SYSTEM

CROSS-REFERENCE TO RELATED APPLICATION

Pursuant to 35 U.S.C. § 119(a), this application claims priority to, and the benefit of the filing date of, European Patent Application Serial No. EP22315016.0, filed Jan. 20, 2022, for "Device for an X-Ray Imaging System," the disclosure of which is hereby incorporated in its entirety herein by this reference.

TECHNICAL FIELD

The present disclosure relates to a device for a tomographic imager, such as an X-ray imaging system, in the field of cone-beam reconstruction techniques (CBCT).

BACKGROUND

In preparation for surgery, such as, for instance, spinal surgery, a patient is placed horizontally on a table on the patient's stomach. A registration phantom is placed on his or her spine and secured to it, near a volume of interest of the patient to be imaged.

BRIEF SUMMARY

According to the present disclosure, the term "near" shall be understood as "at a distance inferior than a predetermined value." The registration phantom is placed on the back of the patient, directly touching the skin or a piece of fabric, which in turn touches the skin of the patient, or secured to a supporting structure that is secured to the bone or the bones, for example an "on-stilt" structure comprising pins implanted into the bone or the bones.

According to the present disclosure, a volume of interest comprises at least part of at least a bone to be imaged and some body tissues around the bone.

For instance, the volume of interest is a part of the patient's spine where the surgery must be realized. The volume of interest is not limited to the spine and relates to any bone, for instance to a knee, the pelvis, a shoulder, etc., of a patient.

The registration phantom, known in itself, is a device that comprises a plurality of radiopaque markers, or fiducials, in this case a set of at least three (3) radiopaque markers, which are arranged in a predefined, known, three-dimensional configuration.

These radiopaque markers can be of any known shape, e.g., spheres, cylinders and so on. Because the three-dimensional configuration of the radiopaque markers is known, they act as landmark on the image detector when illuminated by the X-ray source. For the sake of conciseness, "image detector" is also called "detector" throughout the description. Radiopaque markers of a given registration phantom can be of different shapes.

For each angular position of the c-shaped piece it is then possible to determine the position of the spine within the volume of interest with regard to the registration phantom.

It is possible to compute a 3D image of the volume of interest from the image of the projection of the radiopaque markers on the detector, with reference to the tomographic imager.

Accordingly, even if the patient moves or twists, the surgeon can precisely locate the position of his or her surgical tools with regard to the part of the patient's spine where the surgery must be realized.

When using a CBCT X-ray imaging system, the volume of interest is centered on a piece of bone to be imaged, where the surgery shall be realized. But body tissues around the bone absorb X-ray photons energy.

Accordingly, for a given amount of X-ray energy and a given position of the C-shaped arm, the image on the detector, and especially the image of the registration phantom, differs according to the amount (the thickness) of body tissues within the volume of interest.

The amount of X-ray energy is generally constant for a given volume of interest, that is, for a plurality of positions of the C-shaped arm. Accordingly, for some positions of the C-shaped arm, the amount of X-ray energy may be enough to obtain a usable image on the detector, but for other positions of the C-shaped arm, the amount of X-ray energy may be too low to obtain a usable image on the detector, or too high.

As a consequence, the problem is that, especially when the volume of interest comprises an inhomogeneous distribution of the body tissues around the bone, part of the image obtained on the detector may be unusable, as if burnt by the energy of the X-ray energy when the amount of X-ray energy is too high, especially part of the image corresponding to a null or very low amount of body tissues (typically, the part where the registration phantom lies).

In this context, the present disclosure relates to a device (e.g., a radiopaque device 1000) for a cone-beam (e.g., X-ray beam 411) reconstruction technique X-ray imaging system, the system comprising a cone emitting X-ray source 410 and a plane detector (e.g., plane X-ray detector 420), the X-ray source 410 and the plane detector 420 being integral with one another and movable in rotation in a substantially vertical imaging plane around an axis of rotation and passing through a volume of interest (ROI) of a patient 200 to be imaged, the radiopaque device 1000 comprising:

a registration phantom 100 that comprises a set of at least three radiopaque markers 101 arranged in a known three-dimensional configuration and intended to be placed at a predetermined distance from the volume of interest (ROI) to be imaged, and a set of at least one radiopaque screen 500, integral with the registration phantom 100, and comprising a lower face 503, an internal face 505 oriented toward the registration phantom 100, and an external face 506 opposed to the internal face 505;

the radiopaque device 1000 being configured so that, when it is placed on the patient 200, at least part of the X-rays from the emitting cone that pass from the X-ray source 410 to the plane detector 420 through the registration phantom 100 see their intensity attenuated by passing through the assembly of at least one radiopaque screen 500.

In some embodiments, a plurality of radiopaque screens 500 may be provided, the radiopaque screens 500 being able to be attached two by two (×2) in a removable manner.

In some embodiments, at least two radiopaque screens 500 may be provided and may be attached to one another, in a removable manner, so that they meet at least one of the following characteristics:

the external face 506 of one radiopaque screen 500 is attached to the internal face 505 of the other radiopaque screen 500;

at least one radiopaque screen 500 further comprises an upper face 504, such that the upper face 504 of the radiopaque screen 500 is attached to the lower face 503 of the other radiopaque screen 500.

In some embodiments, at least one radiopaque screen 500 of the assembly is removably attached to the registration phantom 100.

In some embodiments, magnetic fixtures are provided and are configured to removably fix at least two radiopaque screens 500 between them and/or to removably fix at least one radiopaque screen 500 with the registration phantom 100.

In some embodiments, the registration phantom 100 fits into a rectangular parallelepiped, and the height of each radiopaque screen 500 is greater than or equal to the height of the rectangular parallelepiped in which the registration phantom 100 is inscribed.

In some embodiments, at least one radiopaque screen 500 has in cross section, in the imaging plane (YOZ), a vertical gradient of radiopaque material.

In some embodiments, for at least one radiopaque screen 500, at least a part of the internal face 505 is parallel to at least a part of the external face 506.

In some embodiments, at least one radiopaque screen 500 has, in cross section in a plane parallel to the imaging plane, a horn shape whose tip folds over the registration phantom 100 when these are assembled.

In some embodiments, the registration phantom 100 extends along an elongation plane, the assembly of at least one radiopaque screen 500 being perpendicular to the elongation plane, at least at the junction between the radiopaque screen 500 and the registration phantom 100.

In some embodiments, two sets of at least one radiopaque screen 500 are provided, the sets being opposite and symmetrical with respect to a vertical plane perpendicular to the imaging plane passing through the registration phantom 100.

In some embodiments, a single radiopaque screen 500 is provided and has the shape of a dome, optionally with a hole in its top, above the registration phantom 100.

In some embodiments, the set of at least one radiopaque screen 500 is configured so that any X-ray coming from the source of X-rays (e.g., the X-ray source 410) toward the plane detector 420 passing through any of the radiopaque markers 101 of the registration phantom 100 necessarily passes through at least one radiopaque screen 500, either when the line passing through the X-ray source 410 and the plane detector 420 is horizontal plus or minus 10°, or when the thickness of the fat mass of the patient 200 crossed by the X-rays is less than or equal to a predetermined value.

In some embodiments, at least one radiopaque screen 500 is provided with at least one visual indication corresponding to an optimum range of use of the X-ray source 410, the X-ray source 410 comprising an anode and a cathode, the optimum range of use comprising at least one of the values among:
  a maximum value (kV_max) of the voltage between the anode and the cathode of the X-ray source 410;
  a minimum value (kV_min) of the voltage between the anode and the cathode of the X-ray source 410;
  a maximum value (mA_max) of the intensity through the cathode of the X-ray source 410;
  a minimum value (mA_min) of the intensity through the cathode of the X-ray source 410;
  a value (kV_min*mA_min) corresponding to a minimum value (kV_min) of the voltage between the anode and the cathode of the X-ray source 410, multiplied by a minimum value (mA_min) of the intensity across the cathode of the X-ray source 410;
  a value (kV_max*mA_max) corresponding to a maximum value (kV_max) of the voltage between the anode and the cathode of the X-ray source 410, multiplied by a maximum value (mA_max) of the intensity across the cathode of the X-ray source 410.

In some embodiments, the visual indication comprises at least one of the following indications:
  alphanumeric marking;
  a color;
  predetermined graphics.

Other features and advantages of embodiments of the present disclosure will appear in the detailed description that is given as mere illustrative and non-limiting example(s).

BRIEF DESCRIPTION OF THE DRAWINGS

FIG. 11 illustrates an embodiment of a vertical assembly of two radiopaque screens, to increase the height of the resulting assembly.

FIG. 12 illustrates an embodiment of a horizontal assembly of two radiopaque screens, to increase the thickness of the resulting assembly.

DETAILED DESCRIPTION

Figure 1:
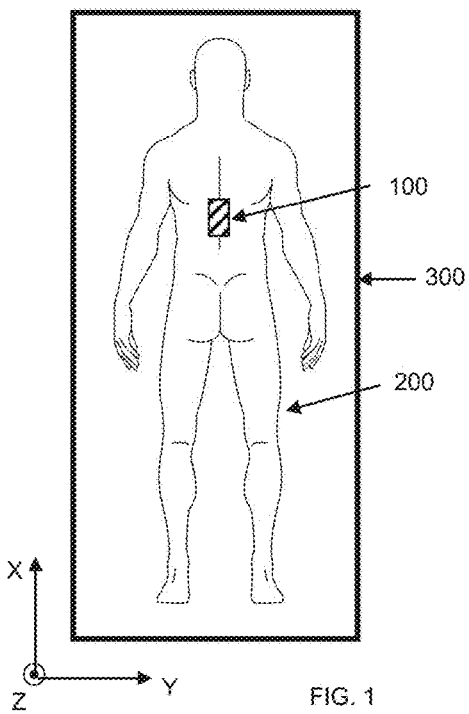
FIG. 1 illustrates a patient lying on his/her stomach on an operating table and equipped with a registration phantom, when viewed from above, according to the prior art.

FIG. 1 illustrates in cross section a patient 200 lying on the patient's stomach on a horizontal table 300, in an XOY plane.

On the patient's back, which serves as a support, a registration phantom 100 has been placed that includes a set of radiopaque markers 101. The registration phantom 100 can have different shapes, each of which fits into a rectangular parallelepiped.

The registration phantom 100 is placed on a substantially horizontal support, typically on the patient's 200 back along the spine. It is placed near a volume of interest ROI of the patient 200 to be imaged, usually directly in contact with the skin. For example, the registration phantom 100 is glued with a biocompatible and radiolucent glue on the patient's 200 skin.

A tomographic imager consists of an X-ray source 410 and a plane detector 420, which are integral with each other, at the extremities of a C-shaped arm 400, which can rotate around a horizontal axis of rotation.

The X-ray source 410 and a plane detector 420 are rotatable in an imaging plane that is substantially vertical, i.e., the YOZ plane on the figures. The patient 200 is lying in a direction parallel to the axis of rotation. In some embodiments, the axis of rotation passes through the volume of interest ROI.

Figure 2:
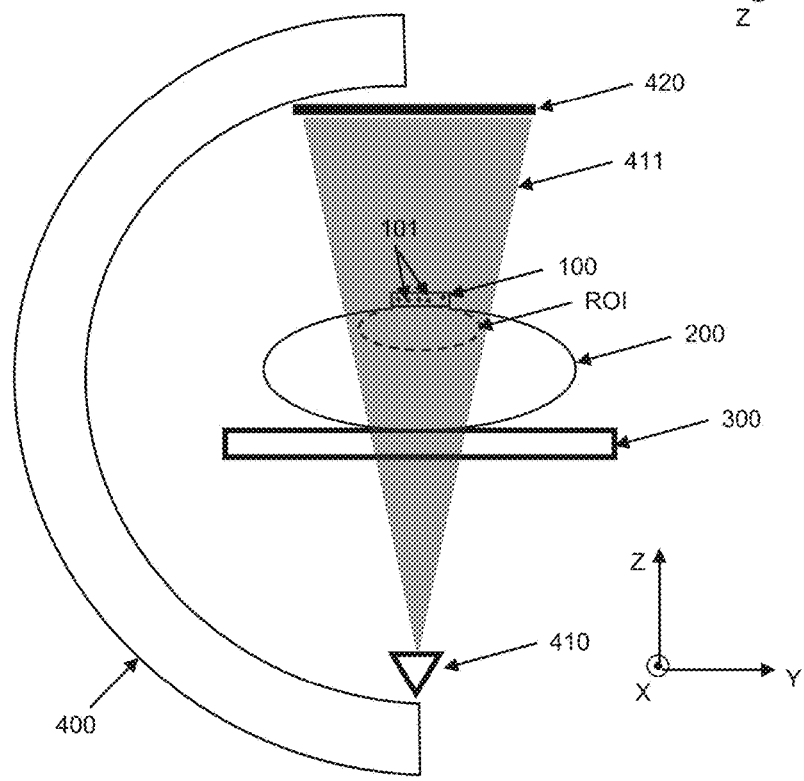
FIG. 2 illustrates, according to the prior art, a cross section in the imaging plane, of the patient of FIG. 1 in a tomographic imager, in which the axis of the X-ray emission cone is vertical.
Figure 3:
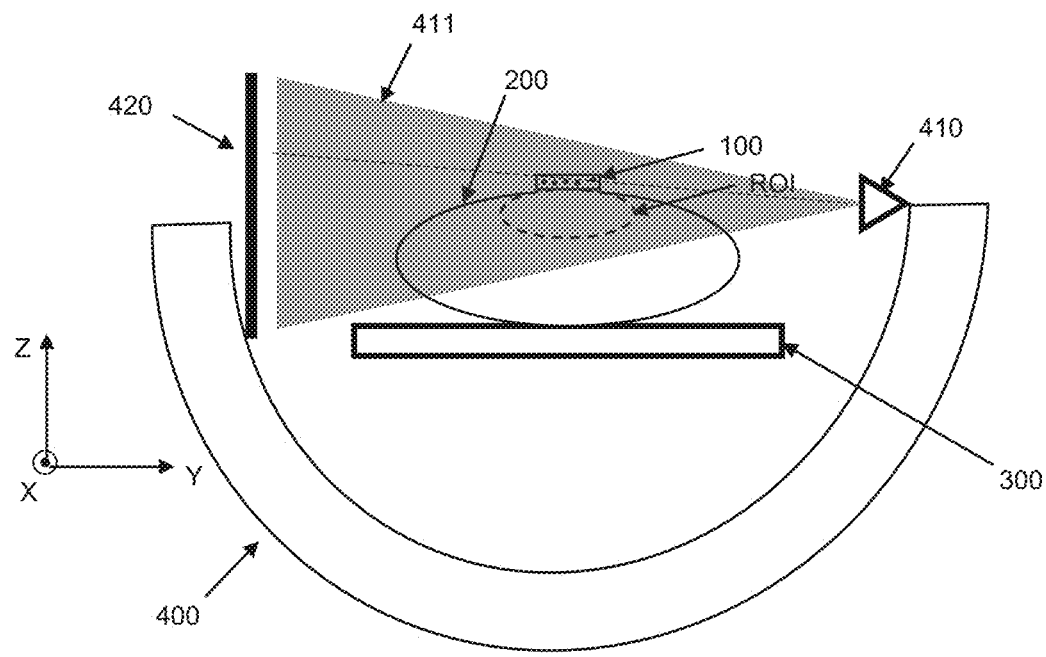
FIG. 3 illustrates, according to the prior art, FIG. 2 in which the axis of the X-ray emission cone is horizontal.

To this end, as illustrated in FIG. 2 and FIG. 3, the X-ray source 410 and the plane detector 420 are, for example, arranged at the ends of a semi-circular arm 400, the arm 400 being movable in rotation about a horizontal axis passing through the center of the circle.

The X-ray source 410 emits X-ray photons, for example, an X-ray beam 411 in the shape of an emission cone of which the X-ray source 410 is the apex, the base being the plane detector 420.

Once the patient 200 is ready for imaging, one can then perform a relative horizontal movement of the tomographic imager and the table on which the patient 200 is placed so that the volume of interest ROI of the patient 200 is included in the emission cone of the X-ray source 410.

A set of images is then taken, each image corresponding to a respective angular position of the arm 400. Typically, to obtain a 3D image, the X-ray source 410 and the plane detector 420 are rotated at least 90° in an imaging plane, which is here a vertical plane, between a starting position and an ending position. For example, for a 90° rotation, the starting position is vertical (FIG. 2), respectively horizontal, and the finishing position is horizontal (FIG. 3), respectively vertical.

In the vertical position, see FIG. 2, the X-rays (e.g., in X-ray beam 411) emitted by the X-ray source 410 pass through part of the patient 200, cover the volume of interest ROI and pass through the registration phantom 100 before reaching the plane detector 420.

For a given power, that is to say for a given value of the intensity through the cathode of the X-ray source 410, the intensity of the X photons is thus attenuated by at least one amongst the table, the patient 200 body and the registration phantom 100, including radiopaque markers 101.

The radiopaque markers 101 are then visible on the image generated on the plane detector 420. The registration phantom 100 comprises at least three, and in this case, at least four non-plane radiopaque markers 101. In this case, the radiopaque markers 101 are spheres, and the registration phantom 100 consists of sixteen spheres, which are inserted, pre-molded into the registration phantom 100.

In a horizontal position, see FIG. 3, the X-rays (e.g., of the X-ray beam 411) emitted by the X-ray source 410 only pass little or not through the table 300, pass little or not through the patient's 200 body, as illustrated by a dotted line on FIG. 3. As a result, the image obtained on the plane detector 420 can be unusable, as if burnt by the energy of the X photons. The position of the radiopaque markers 101 cannot be identified on the image obtained on the plane detector 420.

A solution consisting in reducing the energy, the given value of the intensity through the cathode of the X-ray source 410, is not satisfactory since that amount of energy, i.e., kV the voltage between the anode and the cathode of the X-ray source 410, must be constant for all the images.

To address this problem, a set of at least one radiopaque screen 500 is provided, configured to attenuate the intensity of the X-rays passing through it.

Figure 4:
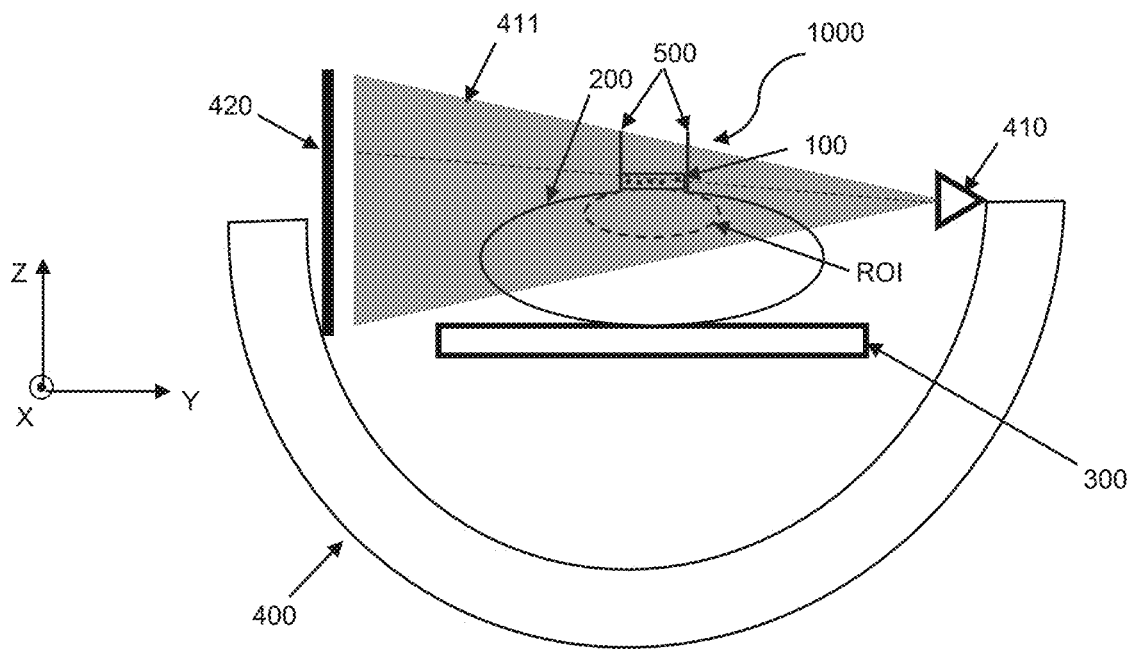
FIG. 4 illustrates FIG. 3 in which the patient is equipped with the device according to embodiments of the disclosure.

The radiopaque screen 500 is configured so that, when it is secured to the registration phantom 100 and placed on the back of a patient 200, at least part of the X-rays that pass from the X-ray source 410 to the plane detector 420 through the registration phantom 100, see their intensity attenuated by passing through the assembly of at least one radiopaque screen 500, as illustrated in FIG. 4.

Preferably, a radiopaque screen 500 is configured such that when it is assembled with the registration phantom 100, any X-ray from the X-ray source 410 toward the plane detector 420 passing through any of the radiopaque markers 101 of the registration phantom 100, necessarily passes through a radiopaque screen 500 when the line passing through the X-ray source 410 and the plane detector 420 is horizontal plus or minus 10°, that is to say when the thickness of the fat mass of the patient 200 crossed by the X-rays is less than or equal to a predetermined value.

For brevity, the set of "at least one radiopaque screen 500" is referred to as the "radiopaque screen 500."

The radiopaque screen 500 includes:
- a lower face 503 (e.g., FIG. 6),
- an internal face 505, or inner face, which in use is oriented toward the registration phantom 100, and
- an external face 506, or outer face, which in use is oriented toward the X-ray source 410, respectively toward the plane detector 420.

The radiopaque screen 500 may further include an upper face 504.

The radiopaque screen 500 may have the shape of a right-angled parallelepiped, or a shape that fits into a right-angled parallelepiped, or when viewed in a transversal plane, in the shape of a triangle or trapezoid shape, or even a horn shape.

Figure 8:
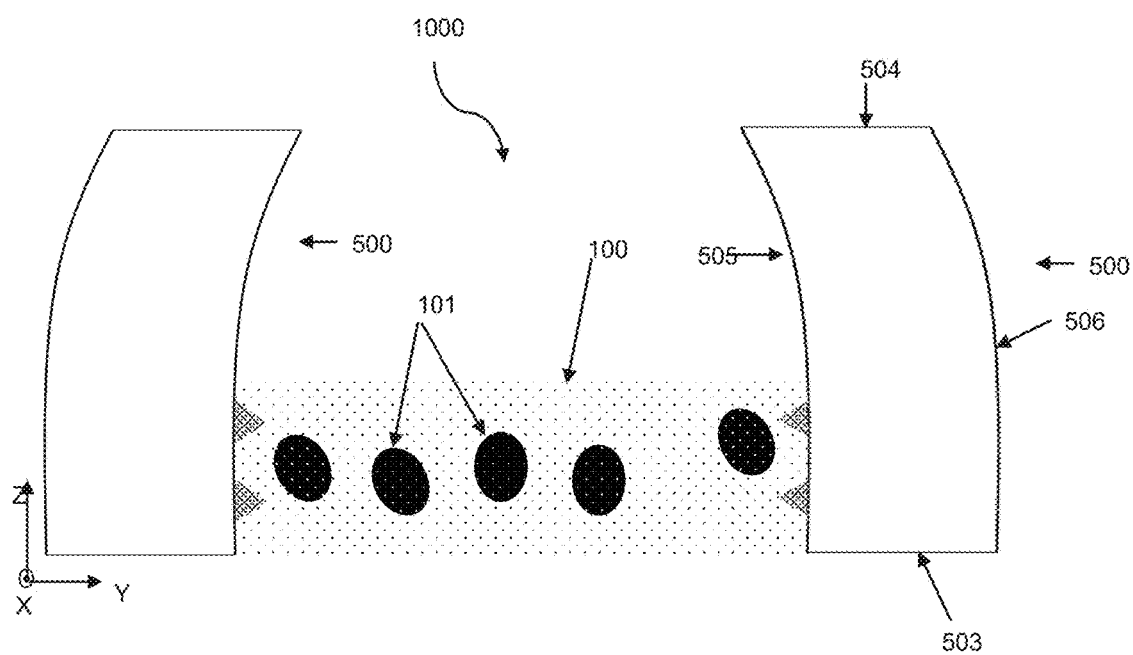
FIG. 8 illustrates an embodiment of the device according to the disclosure in which the radiopaque screens have a curved shape in cross section.

In some embodiments, the radiopaque screen 500 has an inner face 505 parallel to the outer face 506. The shape of the internal face 505, respectively external, can be planar (e.g., as illustrated in particular in FIG. 6) or curved (e.g., as illustrated in FIG. 8), or alternatively a broken line (e.g., as illustrated in FIG. 11 and FIG. 12).

In some embodiments, the radiopaque screen 500 includes a base and a top. In some such embodiments, the base of the radiopaque screen 500 has, in cross section in the imaging plane, a dimension less than or equal to that of its top.

Figure 9:
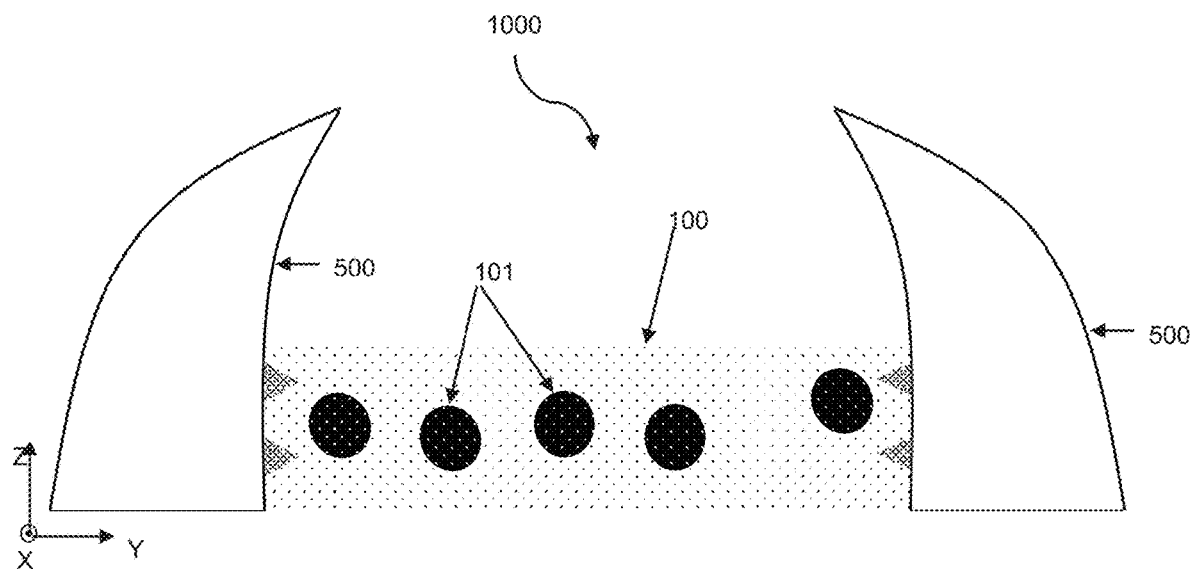
FIG. 9 illustrates an embodiment of the device according to the disclosure in which the radiopaque screens have a horn shape in cross section.

For example, as illustrated in FIG. 9, the radiopaque screen 500 may show, in cross section in the imaging plane, the shape of a horn with the tip bending toward the registration phantom 100 above it.

Figure 10:
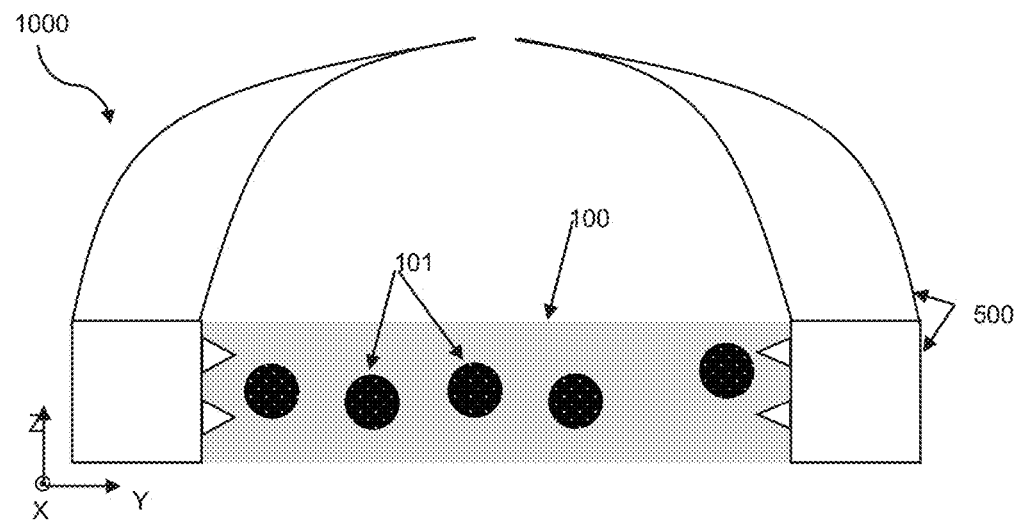
FIG. 10 illustrates an embodiment of the device according to the disclosure in which the radiopaque screens have the shape of a dome, in this case, with a hole at its top.

In some embodiments, such as illustrated in FIG. 10, the radiopaque screen 500 has the shape of a dome, optionally with a hole in its top, and disposed above the registration phantom 100. Preferably, the shape of a dome is symmetrical (e.g., with symmetry of revolution), which facilitates its positioning on the registration phantom 100 since, in this case, its angular position does not matter.

Preferably, the radiopaque screen 500 is integral with the registration phantom 100, at least during the imaging phase. Preferably, the radiopaque screen 500 is removably attached to the registration phantom 100. Thus, it is possible to use several different radiopaque screens 500 for the same registration phantom 100.

Figure 6:
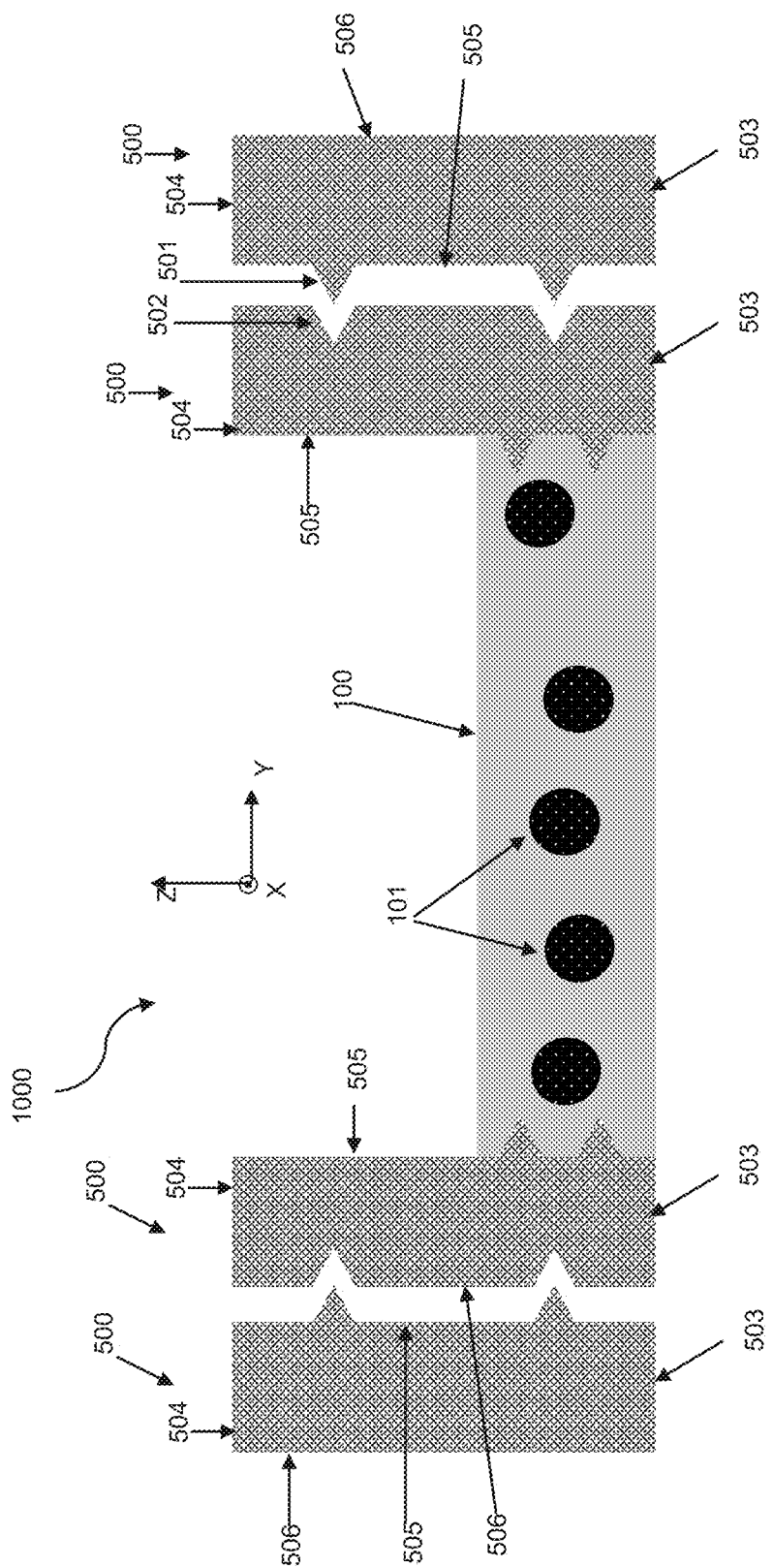
FIG. 6 illustrates an embodiment of the device according to the disclosure in which the radiopaque screens are assembled in pairs on either side of the registration phantom.

In some embodiments, the radiopaque screens 500 can be attached in pairs in a removable manner, as illustrated in FIG. 6. It is thus possible to obtain an assembly of thicker radiopaque screens 500, as illustrated in FIG. 12, and/or higher, as illustrated in FIG. 11, than one of the radiopaque screens 500 constituting the assembly taken on its own, and to decrease the intensity of the X-rays passing through the assembly.

For example, in some embodiments, at least one of the registration phantom 100 and a radiopaque screen 500 includes magnetic attachments (e.g., magnetic fixtures).

For example, in some embodiments, the registration phantom 100 includes magnets and the radiopaque screen 500 includes ferromagnetic elements, or vice versa.

Preferably, when a radiopaque screen 500 comprises a set of at least one magnet, provision is made either for the internal face 505 to be polarized north, respectively south, and that the external face 506 is polarized south, respectively north; or that the upper face 504 is polarized north, respectively south, and that the lower face 503 is polarized south, respectively north, so as to be able to join radiopaque screens 500 two by two (2×2).

The magnetic fixtures are advantageously chosen so that the magnetic force that binds them is such that two radiopaque screens 500, or a radiopaque screen 500 and the registration phantom 100, fixed to one another by the magnetic means, may be separated from each other manually by an adult.

Figure 5A:
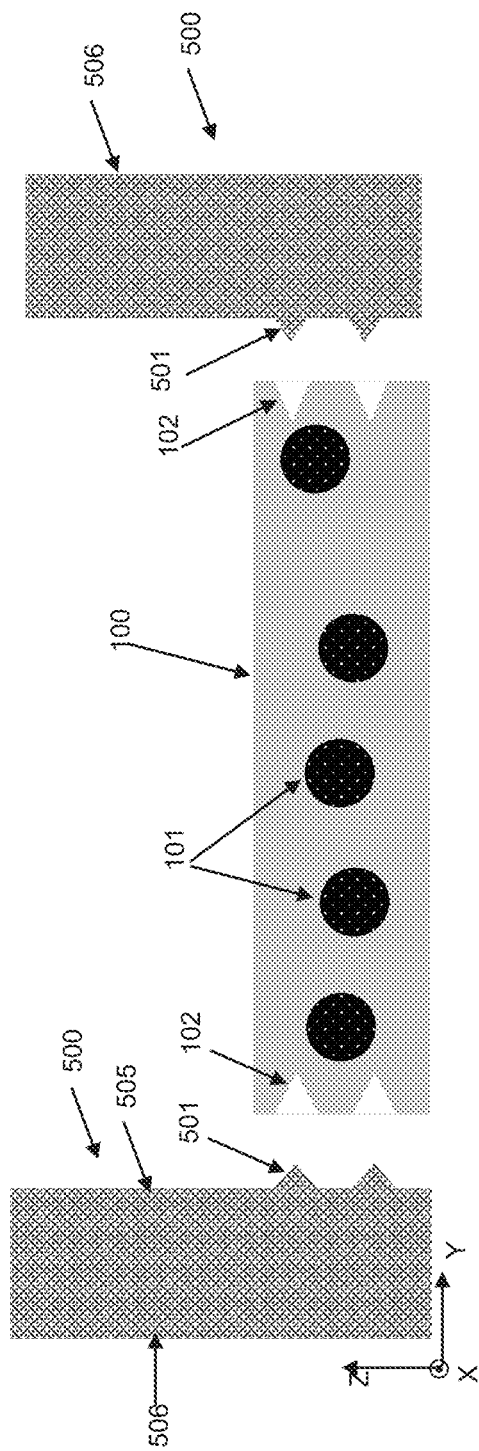
FIG. 5A illustrates an embodiment of the device according to the disclosure, before the assembly of two radiopaque screens with the registration phantom.
Figure 5B:
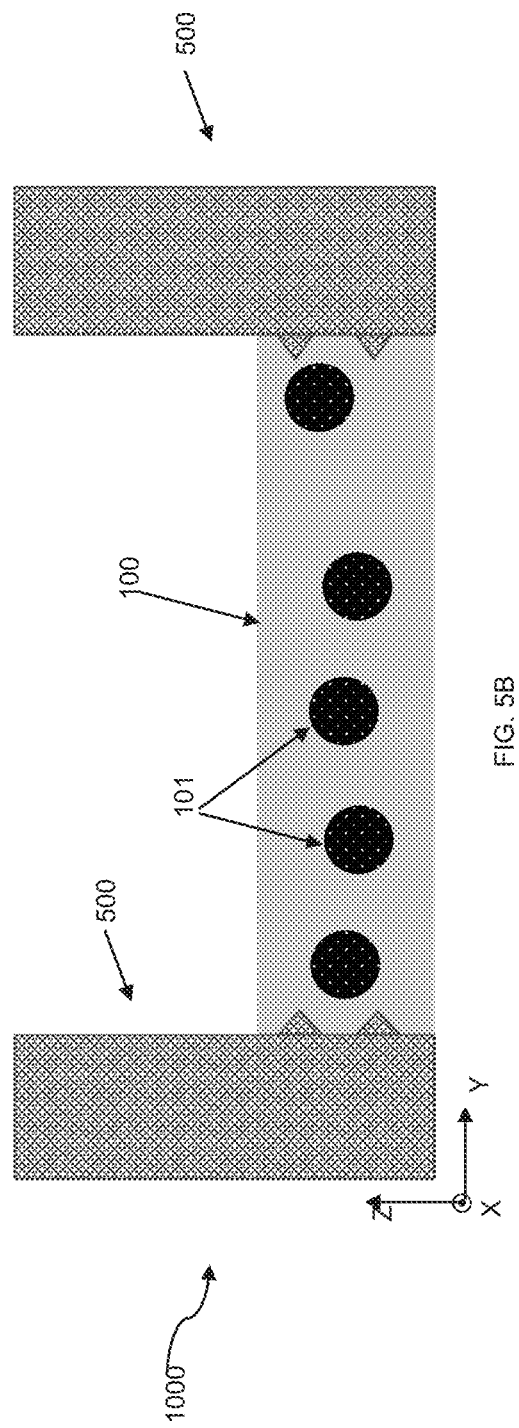
FIG. 5B illustrates an embodiment of the device according to the disclosure, after the assembly of two radiopaque screens with the registration phantom.

Mechanical fastening means can also be provided, for example, in the form of a tenon/mortise, in particular of the LEGO® type (registered trademark) comprising a set of projecting elements 501 configured to fit into corresponding recesses 102 of a registration phantom 100, as illustrated, in particular, in FIG. 5A and FIG. 5B, and/or configured to fit into corresponding recesses 502 (FIG. 6) of another radiopaque screen 500.

In some embodiments, such as illustrated in FIG. 11, the lower face 503 of a first radiopaque screen 500 and the upper face 504 of a second radiopaque screen 500 each have a respective S-shaped or stair-shaped profile, such that the profile of one fits into the profile of the other. It is thus possible to stack the first radiopaque screen 500 and the second radiopaque screen 500, and increase the height of the resulting assembly.

Similarly, as illustrated in FIG. 12, in some embodiments the internal face 505 of a first radiopaque screen 500 and the external face 506 of a second radiopaque screen 500 each have a respective S-shaped or staircase profile, such that the profile of one fits into the profile of the other. It is thus possible to join the first radiopaque screen 500 and the second radiopaque screen 500, and increase the thickness of the resulting assembly.

To decrease the intensity of the X-rays that pass through a radiopaque screen 500, the density of radiopaque material that is comprised within the radiopaque screen 500 may be homogeneous but the thickness of the radiopaque screen 500 may be variable. In this case, the thickness of a radiopaque screen 500 may decrease from bottom to top along the vertical axis as the registration phantom 100 is positioned horizontally. For example, at least one of the inner face 505 and the outer face 506 may be planar (vertical or inclined relative to the vertical), or curved, and in particular elliptical.

Figure 7:
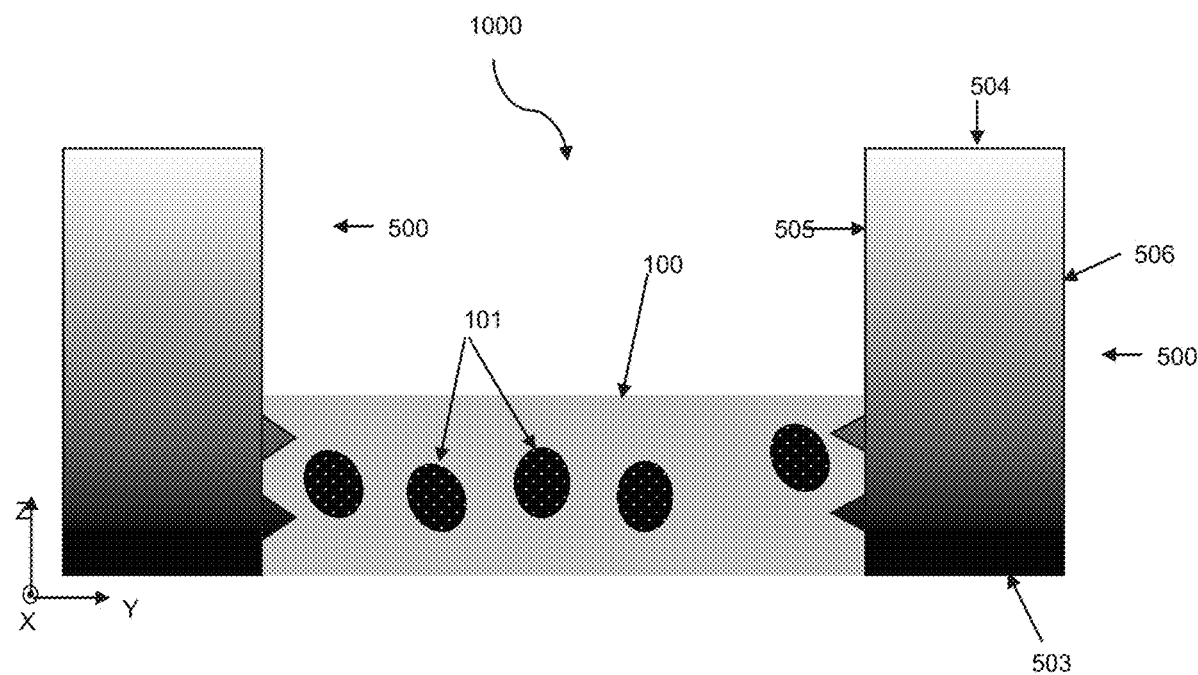
FIG. 7 illustrates an embodiment of the device according to the disclosure in which the radiopaque screens have a gradient of radiopaque material, in this case, along a vertical Z axis.

In some embodiments, the density of radiopaque material of the radiopaque screen 500 may be inhomogeneous and may have at least one gradient, such as a decreasing gradient in the imaging plane, as illustrated in FIG. 7, that is to say according to the vertical axis when the registration phantom 100 is positioned horizontally.

These embodiments can be combined: it can be provided that the thickness of the radiopaque screen 500 is variable and that the density of radiopaque material that it comprises is inhomogeneous.

The radiopaque screen 500 may have a plane of symmetry perpendicular to the imaging plane, therefore a constant thickness in a direction parallel to the axis of rotation.

In some embodiments, the registration phantom 100 extends along an elongation plane, and the radiopaque screen 500 is perpendicular to the elongation plane, at least at the junction therewith, which facilitates the assembly of the radiopaque screen 500 and the registration phantom 100.

In some embodiments, the radiopaque screen 500 is unique and has the shape of a dome, optionally with a hole in its top, above the registration phantom 100, as illustrated in FIG. 10, which represents a cross section of the dome in a plane parallel to the imaging plane.

As all patients 200 do not have the same fat mass and it is necessary to adjust the intensity through the cathode of the X-ray source 410, a plurality of radiopaque screens 500 can be provided, each of which being configured for an optimal range of use.

The optimum range of use is related to the energy of the X-ray source 410 and includes at least one of the following values:
- a maximum value (kV_max) of the voltage between the anode and the cathode of the X-ray source 410;
- a minimum value (kV_min) of the voltage between the anode and the cathode of the X-ray source 410;
- a maximum value (mA_max) of the intensity through the cathode of the X-ray source 410;
- a minimum value (mA_min) of the intensity through the cathode of the X-ray source 410;
- a value (kV_min*mA_min) corresponding to a minimum value (kV_min) of the voltage between the anode and the cathode of the X-ray source 410, multiplied by a minimum value (mA_min) of the intensity across the cathode of the X-ray source 410;
- a value (kV_max*mA_max) corresponding to a maximum value (kV_max) of the voltage between the anode and the cathode of the X-ray source 410, multiplied by a maximum value (mA_max) of the intensity across the cathode of the X-ray source 410.

To illustrate this principle, a radiopaque screen 500 can be provided, the radiopaque material of which may be distributed homogeneously and having the shape of a rectangular parallelepiped.

In some embodiments, for example, the radiopaque material comprises at least one amongst: gold, platinum, tantalum, tungsten, bismuth, barium sulfate, graphene oxide, polymers comprising heavy metal-containing monomers, or polymers comprising iodine/bromine-containing monomers.

Depending on the thickness of the rectangular parallelepiped and/or the density of radiopaque material, the radiopaque screen 500 can more or less attenuate the intensity of the X photons passing through it.

The attenuation capacity of a radiopaque screen 500 can be visually translated by at least one of the following indications:
- an alphanumeric marking;
- a color; and
- a predetermined graphics.

For example, a predetermined color of a radiopaque screen 500, or of a graphic integral with the latter, corresponds to a predetermined range of values [kV_min, kV_max]; [mA_min, mA_max]; [kV_min*mA_min, kV_max*mA_max] of the X-ray source 410.

Nomenclature

100 Registration phantom
101 Radiopaque marker
102 Recess
200 Patient
300 Operating table
400 Semicircular arm of a tomographic imager
410 X-ray source
411 X-ray beam
420 Plane X-ray detector
500 Radiopaque screen
501 Projecting element
502 Recess
503 Lower face
504 Upper face
505 Internal face
506 External face
1000 Radiopaque device
ROI Region of interest

The invention claimed is:

1. A radiopaque device for a cone-beam reconstruction technique X-ray imaging system, the X-ray imaging system comprising a cone emitting X-ray source and a plane detector, the X-ray source and the plane detector being integral with one another and movable in rotation in a substantially vertical imaging plane around an axis of rotation and passing through a volume of interest of a patient to be imaged, the radiopaque device comprising:
a registration phantom comprising a set of at least three radiopaque markers arranged in a known three-dimensional configuration and placeable at a predetermined distance from the volume of interest to be imaged; and
a set of at least one radiopaque screen, integral with the registration phantom, the at least one radiopaque screen comprising:
a lower face;
an internal face oriented toward the registration phantom; and
an external face opposed to the internal face,
the radiopaque device being configured so that, when the radiopaque device is placed on the patient, at least part of X-rays from an emitting cone and that pass from the X-ray source to the plane detector through the registration phantom see their intensity attenuated by passing through the set of at least one radiopaque screen.

2. The radiopaque device of claim 1, wherein the set of at least one radiopaque screen comprises a plurality of the radiopaque screens, the radiopaque screens being attachable two by two in a removable manner.

3. The radiopaque device of claim 2, wherein the plurality of the radiopaque screens comprises at least two of the radiopaque screens attached to one another in the removable manner so that:
the external face of one radiopaque screen is attached to the internal face of another radiopaque screen; and/or
an upper face of one radiopaque screen is attached to the lower face of another radiopaque screen.

4. The radiopaque device of claim 1, wherein at least one radiopaque screen of the set of at least one radiopaque screen is removably attached to the registration phantom.

5. The radiopaque device of claim 1, further comprising magnetic fixtures configured to removably fix at least two radiopaque screens, of the set of at least one radiopaque screen, between the magnetic fixtures and/or to removably fix at least one radiopaque screen, of the set of at least one radiopaque screen, with the registration phantom.

6. The radiopaque device of claim 1, wherein the registration phantom fits into a rectangular parallelepiped, and wherein a height of each radiopaque screen, of the set of at least one radiopaque screen, is greater than or equal to a height of the rectangular parallelepiped in which the registration phantom is inscribed.

7. The radiopaque device of claim 1, wherein at least one radiopaque screen, of the set of at least one radiopaque screen, has in cross section, in the imaging plane, a gradient of radiopaque material.

8. The radiopaque device of claim 1, wherein, for at least one radiopaque screen of the set of at least one radiopaque screen, at least a part of the internal face is parallel to at least a part of the external face.

9. The radiopaque device of claim 1, wherein at least one radiopaque screen, of the set of at least one radiopaque screen, has in cross section in a plane parallel to the imaging plane, a horn shape whose tip folds over the registration phantom when these are assembled.

10. The radiopaque device of claim 1, wherein the registration phantom extends along an elongation plane, the set of at least one radiopaque screen being perpendicular to the elongation plane, at least at a junction between the at least one radiopaque screen and the registration phantom.

11. The radiopaque device of claim 1, wherein the radiopaque device comprises two of the sets of at least one radiopaque screen, the sets of the two being opposite and symmetrical with respect to a vertical plane perpendicular to the imaging plane passing through the registration phantom.

12. The radiopaque device of claim 1, wherein the set of at least one radiopaque screen comprises a single radiopaque screen having a dome shape.

13. The radiopaque device of claim 12, wherein the single radiopaque screen having the dome shape comprises a top defining a hole above the registration phantom.

14. The radiopaque device of claim 1, wherein the set of at least one radiopaque screen is configured so that any X-ray coming from the X-ray source toward the plane detector passing through any of the radiopaque markers of the registration phantom necessarily passes through at least one radiopaque screen of the set of at least one radiopaque screen, either when a line passing through the X-ray source and the plane detector is horizontal plus or minus 10°, or when a thickness of fat mass of the patient crossed by the X-rays is less than or equal to a predetermined value.

15. The radiopaque device of claim 1, wherein at least one radiopaque screen, of the set of at least one radiopaque screen, is provided with at least one visual indication corresponding to an optimum range of use of the X-ray source, the X ray source comprising an anode and a cathode, the optimum range of use comprising at least one value among:
a maximum value (kV_max) of voltage between the anode and the cathode of the X-ray source;
a minimum value (kV_min) of the voltage between the anode and the cathode of the X-ray source;
a maximum value (mA_max) of intensity through the cathode of the X-ray source;
a minimum value (mA_min) of the intensity through the cathode of the X-ray source;
a value (kV_min*mA_min) corresponding to a minimum value (kV_min) of the voltage between the anode and the cathode of the X-ray source, multiplied by a minimum value (mA_min) of the intensity across the cathode of the X-ray source; and a value (kV_max*mA_max) corresponding to a maximum value (kV_max) of the voltage between the anode and the cathode of the X-ray source, multiplied by a maximum value (mA_max) of the intensity across the cathode of the X-ray source.

16. The radiopaque device of claim 15, wherein the at least one visual indication comprises at least one of:

alphanumeric marking;

a color; and predetermined graphics.

* * * * *